United States Patent [19]
Brede

[11] Patent Number: 5,981,853
[45] Date of Patent: Nov. 9, 1999

[54] **TURFGRASS CULTIVARS OF *AGROSITIS IDAHOENSIS***

[75] Inventor: Andrew Douglas Brede, Veradale, Wash.

[73] Assignee: Jacklin Seed Company, Post Falls, Id.

[21] Appl. No.: 08/818,339

[22] Filed: Mar. 14, 1997

[51] Int. Cl.⁶ ............................... A01H 5/10; A01H 5/00; A01H 1/04
[52] U.S. Cl. .......................... 800/320; 800/298; 800/260; Plt./388
[58] Field of Search ........................... 800/200, DIG. 55, 800/235, 298, 320, 260; 47/58, DIG. 1; Plt./90, 388

[56] References Cited

PUBLICATIONS

The Jepson Manual: Higher plants of California. Hickman, Ed. University of California Press, Berkeley, CA. p. 1230, 1993.
Hitchcock. Manual of the Grasses of the United States. Dover Publications, Inc. New York. pp. 334, 349–350, 1971.

*Primary Examiner*—Lynette R. F. Smith
*Assistant Examiner*—Melissa L. Kimball
*Attorney, Agent, or Firm*—Rothwell, Figg, Ernst & Kurz

[57] ABSTRACT

An *Agrostis idatioensis* turfgrass variety is disclosed. The invention relates to the seeds, the plants, and to methods of producing an Agrostis plant having the characteristic of average leaf blade width of less than 1.85 mm wide.

30 Claims, No Drawings

TURFGRASS CULTIVARS OF *AGROSITIS IDAHOENSIS*

This invention relates to the production of novel turfgrass cultivars of Idaho bentgrass (*Agrostis idahoensis* Nash), an obscure grass species that has not been used commercially as turfgrass. Cultivars of the present invention have the improved characteristics of leaf fineness, disease resistance, and turf quality compared to previous Idaho bentgrass genotypes.

BACKGROUND

Homeowners and turfgrass managers in the United States rely on fewer than 20 plant species for all their grassing needs. Moreover, nearly all of these 20 grasses originate from the same general region of Eurasia. An estimated 46.5 million acres of turfgrasses are presently grown in the US (*Grounds Maintenance* magazine, May 1996, p. 10.). Concentrating this few number of species over a vast agricultural landscape is bound to produce problems over time as disease or insect organisms build up and become virulent against existing grasses. This type of pandemic actually occurred in the US in recent years, when large acres of the corn belt were decimated by an outbreak of southern corn leaf blight when a mutated strain of the disease arose.

The solution to this dilemma lies in species diversity. Agriculturists have found that by increasing the number and breadth of species, there is increased genetic diversity and less chance that a particular parasite will devastate a substantial acreage of plants.

Another factor urgently needed is diversity in where species originate. Most of the common turfgrasses grown in this country—Kentucky bluegrass (*Poa pratensis* L.), creeping bentgrass (*Agrostis stolonifera* L.), fine fescue (*Festuca* spp.), tall fescue (*F. arundinacea* Schreb.), and perennial ryegrass (*Lolium perenne* L.)—species that comprise the bulk of turf in the temperate zone—derive from the same region of Europe. Only one turfgrass species originates from here in North America (*Buchloe dactyloides*[Nutt.] Engelm.) and only two from Eastern Asia (*Zoysia japonica* Wild. and *Eremochloa ophiuroides* [Munro.] Hack). To increase the breadth of genetic origin, more turfgrasses are needed that originate from a broader sector of world geography, to bolster the diversity of today's turfgrasses.

Another advantage of developing additional turf species is to help reduce turf maintenance levels. Present-day turfgrasses are better suited to high maintenance than low. They perform best when given a steady diet of water, fertilizer, and chemical pesticides. In theory, grasses native to a particular locale should be able to withstand local growing conditions better than exotics, without the need for additives and preservatives. Grass species that can survive on less input of water or other scarce natural resources offer benefits for reducing maintenance and improving environmental friendliness of lawns.

But finding and developing new grass species from nature is difficult, time consuming, and expensive. The developer must sift through thousands of prospective grasses listed in botanical literature, identify promising grasses, and travel thousands of miles to locate, isolate, identify, transport, quarantine, grow, test, and breed these grasses. This process can take more than 10 years to develop acceptable cultivars. Furthermore, as it turns out, most prospective grasses in nature have no commercial turf value, due to their inability to generate an acceptable ground cover when mowed. The vast majority of natural grasses cannot produce a plush lawn under continuing defoliation.

Also, few grasses found in nature have the ability to produce marketable quantities of seed—a critical necessity for commercialization of a new grass species. Raw germplasm of most native grasses seldom tops 100 lbs. per acre in seed production (R. S. Sadasivaiah and J. Weijer, 1981, The utilization of native grass species for reclamation of disturbed land in the alpine and subalpine regions of Alberta. In Reclamation in mountainous areas. *Proc. 6th ann. meeting Can. Land Reclam. Assoc.*). This level of seed production is not high enough for economic viability. By contrast, popular grasses like tall fescue have been cultivated and selected since prehistoric times for cattle fodder. Only high yielding plant lines have persisted through the ages. Many of today's tall fescue cultivars top 1 ton per acre in seed production.

Yet another complexity facing the plant developer is the unresponsiveness of many wild grasses to plant breeding. The vast majority of wildland grasses lack genetic potential for refinement into desirable turfgrass cultivars. Only after considerable investment in collection and breeding does the developer discover which grass species can be successful bred and which cannot.

The Agrostis genus—better known as the bentgrasses—is comprised of over 100 species, several of which have been developed into successful turfgrasses. One Agrostis in particular, *A. stolonifera* or creeping bentgrass, has become the preeminent grass for golf course putting greens the world over. Another Agrostis species, colonial bentgrass (*A. tenuis* Sibth.), has been bred into a golf course grass useful on tees and fairways in cooler regions. Two or three other Agrostis species find minor turf application, mostly for golf, tennis courts, bowling greens, or an occasional home lawn.

The Agrostis genus is widely distributed throughout the world with representative species found on all of the northern continents. However, of the present-day bentgrass species in use as turfgrasses, all originated from Europe. The original seed of these plants was brought to the US during colonial times.

America has an abundance of native bentgrass species (A. S. Hitchcock, 1951, Manual of the grasses of the United States. USDA Misc. Publ. 200) but none are commercially useable as turf grass.

*Agrostis idahoensis*, or Idaho redtop, was first identified as a distinct species in 1897 when it was first published by Nash in the *Torrey Botany Club Bulletin* 24:42 (Heller 3431). Idaho bentgrass® is the trademarked name registered for this grass species by Jacklin Seed Company of Post Falls, Id.

*Agrostis idahoensis* is found in nature throughout the mountains of New Mexico, Arizona, and California, along the Rockies, and north to Fairbanks, Ak. *Agrostis idahoensis* is a bunch-type perennial grass, lacking lateral runners. Commercial bentgrass species (creeping bentgrass, colonial bentgrass, etc.) all possess stolons (above-ground running stems) and/or rhizomes (below ground running stems). Hitchcock describes *Agrostis idahoensis* as follows:

> Culms slender, tufted, 10 to 30 cm tall, leaves mostly basal, the blades narrow; panicle loosely spreading, 5 to 10 cm long, the branches capillary, flexuous, minutely scabrous; spikelets 1.5 to 2.5 mm long; lemma about 1.3 mm long, awnless; palea minute. Differs from *A. scabra* in the smaller spikelets and in the narrower panicle with shorter flexuous branches.

Piper and Beattie (Charles V. Piper and R. Kent Beattie, 1914, Flora of Southeastern Washington and adjacent Idaho, New Era Printing Co., Lancaster, Pa.) studied the natural occurrence of *Agrostis idahoensis*. They found it common to the alpine woods of the Craig Mountains. Their botanical description is as follows:

Delicate, loosely-tufted, glabrous, perennial, 10–30 cm high; blades flat, narrow, 1–6 cm long; panicle loose, green or purple, 5–10 cm long; rays capillary; spikelets about 1.5 mm long; lower glume scabrous on the keel, slightly larger than the upper; lemma truncate, awnless, 1 mm long; palea minute.

Correll and Correll (D. S. Correll and H. B. Correll, 1972, Aquatic and wetland plants of the Southwestern United States, Stanford Univ. Press, Stanford, Calif.) reported that *Agrostis idahoensis* is an important native wetland species in moist mountain meadows, swamps, shallow water of ponds, lakes, along streams, and on sand-gravel bars in river beds throughout the West. DeBenedetti and Parsons (S. H. DeBenedetti and D. J. Parsons, 1984, Postfire succession in a Sierran subalpine meadow, *Amer. Midland Naturalist* 111: 118–125) concluded that *Agrostis idahoensis* was the most important native grass species present in post-fire succession of subalpine grasslands in California. Its tenacious growth under adverse conditions makes it a valuable forage for wildlife.

In the mining districts of Northern Idaho, native stands of near 100% *Agrostis idahoensis* exist, where other grasses and forbs have long been eradicated through the continued runoff of mine pollution. *Agrostis idahoensis* is one of the few plants capable of surviving and prospering under these loads of heavy metals, making *Agrostis idahoensis* potentially valuable for reclamation of similarly affected sites.

SUMMARY OF THE INVENTION

The present invention provides for the development of novel cultivars of grass species never before exploited for turf purposes. Cultivars developed from this species demonstrate enhanced turfgrass properties, including improvements in disease tolerance, density, fineness of leaf, and overall turfgrass quality.

More specifically, the present invention relates to an *Agrostis idahoensis* plant having the characteristics of an average leaf blade width of less than 1.85 mm under turf-maintained conditions.

The present invention further relates to an *Agrostis idahoensis* plant having an average shoot density of greater than 2.7 shoots per cm$^2$ under turf-maintained conditions.

The invention further relates to a method of making an $F_1$ hybrid by crossing the plant of the present invention with another Agrostis plant.

DEFINITIONS

In the description and tables which follow, a number of terms are used. In order to provide a clear and consistent understanding of the specification and claims, including the scope to be given such terms, the following definitions are provided:

Average Leaf Blade Width

As used herein, the term average leaf blade width means the leaf blade width as measured in millimeters and is determined as follows: Turf plots are grown and maintained in the manner described for evaluation of turf quality. After one year of growth and maintenance, sections of sod 2 inches by 5 inches are cut and removed from the plot by randomly selecting a representative surface area. Four plugs are removed per plot. Blade width of the second and third youngest leaves per tiller (vertical shoot) are measured on all plants in the 2 by 5 inch area. The youngest leaf occurs at the top of the tiller, with older ones successively down the shoot. The leaf blade width is measured in millimeters across the widest part of the blade, with any creasing of the blade pressed out.

Average Shoot Density

As used herein, the term average shoot density means the number of grass shoots measured in four plugs. During the process of blade width measurement, the number of grass shoots for each genotype are counted in the four plugs of 2 by 5 inch area. A grass shoot is defined as an autonomous unit possessing a vertical sheath segment, and a minimum of two leaves, including the vertical or bud leaf. Shoot counts per plug are converted numerically into shoots per cm$^2$, based on the exact measured area of the plug.

Brown Patch

The term brown patch means the level of disease on the plants. Brown patch is a foliar plant disease incited by the *Rhizoctonia solani* fungus. Brown patch severity is evaluated visually on a 1 to 9 integer rating scale, in a manner similar to turfgrass quality. Symptoms are evaluated during a naturally occurring field disease epidemic. With brown patch evaluation, a rating of 1 would indicate complete necrosis from the disease, 5 would be moderate damage, and 9 would be complete resistance to the disease. Ratings are taken when the turf is actively growing, when regular mowing is taking place, and when no stresses such as drought or other diseases are apparent.

Leaf Color

The term leaf color means that the leaf color is evaluated visually on a 1 to 9 integer rating scale, in a manner similar to turfgrass quality. With leaf color evaluation, a rating of 1 would equate to yellow-green turf, 5 to average green turf, and 9 to intensely dark green turf color. Ratings are taken when the turf is actively growing, when regular mowing is taking place, and when no stresses such as drought or disease are apparent.

Leaf Texture

The term leaf texture means that the leaf texture is evaluated visually on a 1 to 9 integer rating scale, in a manner similar to turfgrass quality. With leaf texture evaluation, a rating of 1 would equate to coarse, broad-bladed turf, 5 to turf of an average blade width and 9 to turf of extremely fine blade width. Ratings are taken when the turf is actively growing, when regular mowing is taking place, and when no stresses such as drought or disease are apparent.

Net Blotch the term net blotch disease is incited by the *Drechslera/Bipolaris* spp. fungas. Net blotch severity is evaluated visually on a 1 to 9 integer rating scale, in a manner similar to turfgrass quality. Symptoms are evaluated during a naturally occurring field disease epidemic. With net blotch evaluation, a rating of 1 would indicate complete necrosis from the disease, 5 would be moderate damage, and 9 would be complete resistance to the disease. Ratings are taken when the turf is actively growing, when regular mowing is taking place, and when no stresses such as drought or other diseases are apparent.

Seedling Vigor the term seedling vigor means the level of emergence and vigor expressed by the seedlings. Seedling vigor is evaluated visually on a 1 to 9 integer rating scale, in a manner similar to turfgrass quality. With seedling vigor evaluation, ratings are taken 4 weeks after seed establishment, approximately 14 days from the date when the first seedlings are observed protruding above the soil surface. A rating value of 1 would equate to the complete lack of seedling emergence, 5 would indicate an average emergence value, and 9 would indicate extremely vigorous seedling establishment—essentially a complete ground coverage by the turf. Ratings are taken when the turf is actively growing, when no stresses such as drought or disease are apparent. It is assessed just prior to the stand's first mowing.

Significant Difference

As used in the tables, the indication of "*", "", and "*" asterisks indicate significant differences at the $p \leq 0.05$, 0.01, and 0.001 levels, respectively.

Turfgrass Quality

As used herein, the term turfgrass quality means that to evaluate turfgrass quality, grasses are seeded into plots 4 by 6 feet, 5 by 5 feet or similar, at a seeding rate (seed grams per square meter) equal to commercial rates listed in turf textbooks. Plots are maintained under fertilization and watering to minimize stress, and at a weekly mowing height of ¾ to 1½ inch. Four plots of Variety A are planted in a randomized complete block design arrangement with four plots of Variety B. Visual ratings are taken monthly during the growing season on a 1 to 9 rating scale, with 1 equal to bare ground, 2 equal to thin, brown turf, 3 equal to substandard turf, 4 equal to marginally acceptable turf, 5 equal to average turf, 6 equal to slightly above average turf, 7 equal to dense, robust turf, 8 equal to turf of exception recorded and 9 is equal to ideal turf quality. Ratings are conducted by a university-trained specialist with a graduate degree in Turfgrass Science. Monthly data ratings are analyzed using a statistical procedure known as the analysis of variance and either a t-test or LSD test, at the 0.05 level of probability. A significant analysis indicates the two varieties, A and B, are different, and that the difference is not due to random error or natural plant and soil variability. A non-significant analysis would indicate that the varieties A and B were indistinguishable in turf quality and could be considered to be identical.

Vegetative Propagules

As used herein, the term vegetative propagules means sprigs, plugs, stolons and sod.

DETAILED DESCRIPTION OF THE INVENTION

The novel turfgrass cultivars and methods developed by this invention may be produced by following the detailed descriptions listed below. The process began with identification of species with turfgrass potential through an exhaustive search of the botanical literature. Numerous promising grass species were identified, located, tested, and rejected before *A. idahoensis* was entered into plant breeding. The *A. idahoensis* selections were then further developed using modified recurrent selection. A series of superior cultivars were obtained with enhanced turfgrass characteristics and performance. The improvements instilled into these cultivars are quantifiable and distinctive. Previous genotypes perform poorly as mowed turf, if they survive at all. The enhanced cultivars of the present invention perform competitively with other popular turf cultivars.

Cultivars of the present invention developed from these *Agrostis idahoensis* will enhance the presently narrow genetic range of species grown for turf. Additionally the characteristics of tolerance to salt, heavy metals, and drought offer interesting prospects for application under adverse growing conditions. The use of the present invention results in savings of water, fertilizer, and pesticide over present-day turfgrasses.

This present invention identifies *Agrostis idahoensis* as a wildland species that is capable of being bred into useful turfgrass cultivars, out of the thousands of possible grass plants found in nature. Having the superior *Agrostis idahoensis* cultivars of the present invention allows breeders to develop similar commercial cultivars of these species without going through the lengthy painstaking process of identifying, locating, selecting and testing the potential grass species.

Starting in June, 1987, native plants of *Agrostis idahoensis* were collected from the river basins of Northern Idaho in the hard-rock mining district. Subsequent collecting trips added more germplasm as shown in Table 1.

TABLE 1

| Year | Number of introductions |
|------|-------------------------|
| 87   | 2                       |
| 88   | 7                       |
| 89   | 223                     |
| 90   | 14                      |
| 91   | 138                     |
| 92   | 103                     |
| 93   | 131                     |
| 94   | 64                      |

Promising plants were identified in the wild, and seed was cut from their seedheads. Seed of collected plants was harvested, threshed, and sown into turf observation plots in Post Falls, Id., beginning in 1989, and in every year thereafter. Plots were maintained as lawn turf with normal mowing, watering, and fertilization comparable to that of a home lawn. Entries that prospered were identified by averaging monthly turf quality ratings over the span of the trial.

Plants of top entries were dug from the plots, sprigged into greenhouse flats, and later established in a spaced-plant field nursery for observation. After one year's growth, attractive, disease-free plants were dug up from the nursery just prior to flowering and transported to an isolated site for pollination with other top entries which had similar plant characteristics.

Each plant in these isolation blocks was harvested individually, threshed, and sown into a subsequent set of turf plots as before. In each successive breeding generation, improved entries were compared along side plots of unimproved *Agrostis idahoensis* and plots of 'Streaker' redtop, a standard cultivar of *A. gigantea* Roth.

Three initial improved cultivars were developed from this *Agrostis idahoensis* breeding program: 'J-100' (now named 'GolfStar'), 'J-101,' and 'J-102.' Visual ratings and botanical measurements were taken from the improved cultivars and were compared to various unimproved *Agrostis idahoensis* introductions, which represented unimproved plants derived directly from nature without breeding. Tables 2, 3 and 4 summarizes the data of these comparisons. Data were analyzed using analysis of variance and unpaired t-tests to determine statistical differences between the groups. The genetic improvements in *A. idahoensis* of the present invention are: 1) Improved, darker green leaf color; 2) finer (i.e., narrower) leaf blades; 3) better resistance to net blotch/leafspot disease (incited by *Drechslera/Helminthosporium* spp.); 4) improved seedling vigor; 5) enhanced turfgrass quality; and 6) a higher shoot density which indicates plants were denser and better adapted for turf use.

Table 2 shows visual turf characteristics evaluated in Poolesville, Md., on improved Idaho bentgrass (*Agrostis idahoensis* Nash) versus unimproved, raw germplasm collected from nature (Shoshone County, Id., 1990–91). 'Streaker' redtop (*A. gigantea*) is offered as a reference standard. The trial was established in September, 1995 and was evaluated throughout the 1996 growing season under turf-maintained conditions.

The improved and unimproved Idaho bentgrasses in Table 2 each represent means from several sources. The improved sources were from three cultivars developed by Jacklin Seed Company. The unimproved sources originated from germplasm obtained from US native populations: Improved Idaho bentgrass varieties include: GolfStar (J-100), J-101, J-102. The unimproved Idaho bentgrass germplasm sources are: 90-0238, 90-0825, 91-0170, 91-0175, and 91-0228.

All variables were visually rated on a 1 to 9 scale, with 9 equaling good quality, dark color, fine leaf texture, or no disease.

improved sources were from three cultivars developed by Jacklin Seed Company. The unimproved sources originated from germplasm obtained from US native populations: Improved Idaho bentgrass varieties include: GolfStar (J-100), J-101, J-102. Unimproved Idaho bentgrass germplasm sources: 93-0083, 93-0084, 93-0085, 93-0086, 93-0087, 93-0088, 93-0089, 93-0090, 93-0091, 93-0092, 93-0093, 93-0094, 93-0095, 93-0096, 93-0097, 93-0098, 93-0099, 93-0100, 93-0101, 93-0102, 93-0103, 93-0104, 93-0105, 93-0106, 93-0107, 93-0108, 93-0109, 93-0110, 93-0111, 93-0112, 93-0113, 93-0114, 93-0115, 93-0116, 93-0117, 93-0118, 93-0119, 93-0120, 93-0121, 93-0122, 93-0123, 93-0124, 93-0125, 93-0126, 93-0127, 93-0128, 93-0129, 93-0130, 93-0131, 94-0012, 94-0013, 94-0014, 94-0015, 94-0016, 94-0017, 94-0018, 94-0019, 94-0020, 94-0021, 94-0022, 94-0023, 94-0024, 94-0025, 94-0026, 94-0027, 94-0028, 94-0029, 94-0030, 94-0031, 94-0032,

TABLE 2

| | Leaf and disease ratings | | | | Turfgrass quality | | | | | |
| --- | --- | --- | --- | --- | --- | --- | --- | --- | --- | --- |
| | Leaf color | Leaf texture | Net blotch disease | Brown patch disease | | | | | | |
| Group | April | April | May | July | January | April | May | July | August | Mean |
| Improved Idaho bentgrass | 4.4 | 5.5 | 7.4 | 5.2 | 6.7 | 5.7 | 6.0 | 4.8 | 5.0 | 5.6 |
| Unimproved Idaho bentgrass | 3.0** | 3.6* | 4.1*** | 4.2 | 3.0*** | 3.3* | 2.6*** | 3.3 | 3.3*** | 3.1*** |
| Streaker redtop | 2.0** | 3.0 | 2.0** | 2.0* | 1.0*** | 2.5* | 1.0*** | 1.0* | 1.0*** | 1.3*** |

Table 3 shows visual turf quality evaluated in Post Falls, Id., on improved Idaho bentgrass (*Agrostis idahoensis* Nash) versus unimproved, raw germplasm collected from nature (Shoshone and Bonner County, Id., 1993–94). 'Streaker'

94-0033, 94-0034, 94-0035, 94-0036, 94-0037, 94-0038, 94-0039, 94-0040, 94-0041.

All variables were visually rated on a 1 to 9 scale, with 9 equaling good quality or seedling vigor.

TABLE 3

| Group† | Seeding vigor October 1994 | Quality May 1995 | Quality June 1995 | Quality July 1995 | Quality August 1995 | Quality October 1995 | Quality November 1995 | Quality May 1996 | Quality July 1996 | Quality September 1996 | Quality October 1996 | Quality Mean |
| --- | --- | --- | --- | --- | --- | --- | --- | --- | --- | --- | --- | --- |
| Improved Idaho bentgrass | 8.3 | 7.0 | 6.7 | 6.7 | 6.0 | 5.3 | 5.7 | 3.7 | 4.7 | 6.7 | 5.3 | 5.8 |
| Unimproved Idaho bentgrass | 5.2* | 3.6*** | 2.2*** | 2.6*** | 2.4*** | 3.2*** | 2.0*** | 2.3* | 2.5*** | 2.0*** | 2.1*** | 2.5*** |
| Streaker redtop | 8.3 | 2.6* | 2.5* | 1.5* | 1.5* | 1.4* | 1.1* | 1.1 | 2.0* | 1.9* | 2.0* | 1.8*** | redtop (*A. gigantea*) is offered as a reference standard. The trial was established in September 1994 and was evaluated throughout the 1995 and 1996 growing seasons under turf-maintained conditions.

The improved and unimproved Idaho bentgrasses in this table each represent means from several sources. The Table 4 shows leaf and plant measurements of improved Idaho bentgrass (*Agrostis idahoensis* Nash) versus unimproved, raw germplasm collected from nature (Shoshone County, Id., 1990–91). The trial was established September, 1995 in Poolesville, Md., and September, 1994 in Post Falls, Id., and was maintained under mowed, turf conditions. Sample plugs were pulled from plots on Aug. 28, 1996 for density and leaf readings. Four plugs were measured per genotype.

The Idaho bentgrasses in this table represent means from several sources. The improved source was from a cultivar developed by Jacklin Seed Company. The unimproved sources originated from germplasm obtained from US native populations: Improved Idaho bentgrass variety include: GolfStar (J-100). Unimproved Idaho bentgrass germplasm sources are: 90-0236, 91-0170, 91-0228 (Maryland); and 91-0228 (Idaho).

TABLE 4

| Group† | Leaf width (mm) | | Shoot density (shoots/cm$^2$) | |
| --- | --- | --- | --- | --- |
| | Maryland | Idaho | Maryland | Idaho |
| Improved Idaho bentgrass | 1.5 | 1.8 | 4.1 | 2.9 |
| Unimproved Idaho bentgrass | 1.9*** | 2.1*** | 2.6*** | 1.9* |

Deposit Information

*Agrostis idahoensis* J100 seed of this invention has been placed on deposit with the American Type Culture Collection (ATCC), Manassas, Va. 20110, under Deposit Accession Number PTA-245 on Jun. 18, 1999; *Agrostis idahoensis* J101 has been deposited with the American Type Culture Collection of Manassas, Va. under Deposit Accession Number PTA-246 on Jun. 18, 1999 and *Agrostis idahoensis* J102 has been deposited with the American Type Culture Collection of Manassas, Va. under Deposit Accession Number PTA-247 on Jun. 18, 1999.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An *Agrostis idahoensis* seed designated J-100, wherein a sample of said seed has been deposited with the American Type Culture Collection under ATCC Accession No. PTA-245.

2. The plant or its parts produced by the seed of claim 1.

3. Pollen of the plant of claim 2.

4. An ovule of the plant of claim 2.

5. Vegetative propagules of the plant of claim 2.

6. An *Agrostis idahoensis* plant having all of the physiological and morphological characteristics of the *Agrostis idahoensis* plant of claim 2.

7. A method for producing a hybrid *Agrostis idahoensis* seed comprising crossing a first parent *Agrostis idahoensis* plant with a second parent *Agrostis idahoensis* plant and harvesting the resultant hybrid *Agrostis idahoensis* seed, wherein said first or second parent *Agrostis idahoensis* plant is the *Agrostis idahoensis* plant of claim 2.

8. A hybrid seed produced by the method of claim 7.

9. A hybrid plant or its parts produced by growing said hybrid *Agrostis idahoensis* seed of claim 8.

10. Vegetative propagules of the plant of claim 9.

11. An *Agrostis idahoensis* seed designated J-101, wherein a sample of said seed has been deposited with the American Type Culture Collection under ATCC Accession No. PTA-246.

12. The plant or its parts produced by the seed of claim 11.

13. Pollen of the plant of claim 12.

14. An ovule of the plant of claim 12.

15. Vegetative propagules of the plant of claim 12.

16. An *Agrostis idahoensis* plant having all of the physiological and morphological characteristics of the *Agrostis idahoensis* plant of claim 12.

17. A method for producing a hybrid *Agrostis idahoensis* seed comprising crossing a first parent *Agrostis idahoensis* plant with a second parent *Agrostis idahoensis* plant and harvesting the resultant hybrid *Agrostis idahoensis* seed, wherein said first or second parent *Agrostis idahoensis* plant is the *Agrostis idahoensis* plant of claim 12.

18. A hybrid seed produced by the method of claim 17.

19. A hybrid plant or its parts produced by growing said hybrid *Agrostis idahoensis* seed of claim 18.

20. Vegetative propagules of the plant of claim 19.

21. An *Agrostis idahoensis* seed designated J-102, wherein a sample of said seed has been deposited with the American Type Culture Collection under ATCC Accession No. PTA-247.

22. The plant or its parts produced by the seed of claim 21.

23. Pollen of the plant of claim 22.

24. An ovule of the plant of claim 22.

25. Vegetative propagules of the plant of claim 22.

26. An *Agrostis idahoensis* plant having all of the physiological and morphological characteristics of the *Agrostis idahoensis* plant of claim 22.

27. A method for producing a hybrid *Agrostis idahoensis* seed comprising crossing a first parent *Agrostis idahoensis* plant with a second parent *Agrostis idahoensis* plant and harvesting the resultant hybrid *Agrostis idahoensis* seed, wherein said first or second parent *Agrostis idahoensis* plant is the *Agrostis idahoensis* plant of claim 22.

28. A hybrid seed produced by the method of claim 27.

29. A hybrid plant or its parts produced by growing said hybrid *Agrostis idahoensis* seed of claim 28.

30. Vegetative propagules of the plant of claim 29.

* * * * *